United States Patent [19]

Hasspacher

[11] Patent Number: 4,609,664

[45] Date of Patent: Sep. 2, 1986

[54] ANTIASTHMATIC PIPERIDYLIDENE DERIVATIVES

[75] Inventor: Klaus Hasspacher, Riehen, Switzerland

[73] Assignee: Sandoz Ltd., Basel, Switzerland

[21] Appl. No.: 631,221

[22] Filed: Jul. 16, 1984

Related U.S. Application Data

[63] Continuation of Ser. No. 499,371, May 31, 1983, abandoned, which is a continuation of Ser. No. 296,912, Aug. 27, 1981, abandoned.

[30] Foreign Application Priority Data

Sep. 2, 1980 [CH] Switzerland .................. 6606/80

[51] Int. Cl.$^4$ .................. A61K 31/445; C07D 409/08
[52] U.S. Cl. .................. 514/324; 514/325; 546/197; 546/198; 546/200; 546/202; 546/203; 546/204
[58] Field of Search .............. 546/197, 198, 200, 202, 546/203, 204; 424/263, 267; 514/324, 325

[56] References Cited

U.S. PATENT DOCUMENTS

| | | | |
|---|---|---|---|
| 4,128,549 | 12/1978 | Bourquin et al. | 546/202 |
| 4,273,780 | 6/1981 | Waldvogel et al. | 546/202 X |

FOREIGN PATENT DOCUMENTS

| | | | |
|---|---|---|---|
| 746508 | 11/1966 | Canada | 546/203 |
| 780441 | 3/1968 | Canada | 546/202 |
| 2256392 | 5/1973 | Fed. Rep. of Germany | 546/202 |
| 1488972 | 7/1967 | France | 546/203 |
| 1117259 | 6/1968 | United Kingdom | 546/203 |

OTHER PUBLICATIONS

Chemical Abstracts, 69:86820b (1968) [Jucker, E., et al., France 1,499,847, 10/27/67].
Chemical Abstracts, 74:125672e (1971) [Jucker, E., et al., France M. 6269, 9/30/68].
Carissimi et al., J. Med. Chem., 8, 542 (1965).
Engelhardt, E., et al., J. Med. Chem., 8(6), 829 (1965).
Physicians' Desk Reference, 39th Ed., p. 1342.

Primary Examiner—Richard A. Schwartz
Attorney, Agent, or Firm—Gerald D. Sharkin; Robert S. Honor; Thomas O. McGovern

[57] ABSTRACT

Piperidylidene derivatives of formula

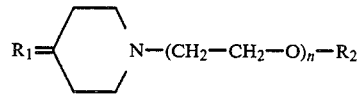

wherein n is 2 or 3, $R_1$ comprises a tricyclic nucleus and $R_2$ is hydrogen or an acid residue, useful in the treatment and prophylaxis of asthmatic conditions.

11 Claims, No Drawings

ANTIASTHMATIC PIPERIDYLIDENE DERIVATIVES

This is a continuation of application Ser. No. 499,371 filed May 31, 1983, now abandoned, which in turn is a continuation of application Ser. No. 296,912 filed Aug. 27, 1981, now abandoned.

The present invention relates to piperidylidene derivatives, their production and pharmaceutical compositions containing them.

In accordance with the invention, there are provided compounds of formula I

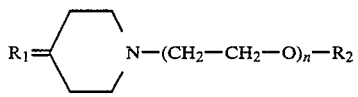

wherein
n is 2 or 3,
$R_1$ comprises a tricyclic nucleus of formula Z

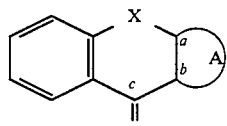

in which X is —S—, —$CH_2$—$CH_2$—, —CH=CH— or —$CH_2$—CO— —$CH_2$—C(=NOH)— or —$CH_2$—CH(OH)— in which the oxo, oxime or hydroxy group is attached to the carbon atom adjacent to a, and A is a fused benzene ring, a fused thiophene ring in which the sulfur atom is adjacent to a, or a fused pyridine ring in which the nitrogen atom is adjacent to b, and $R_2$ is hydrogen or a physiologically-acceptable and -hydrolysable acid residue, as well as the acid addition salts thereof.

In the compounds of formula I, the substituent $R_1$ is attached to the piperidylidene ring directly via the double bond at the carbon atom c.

Compounds of formula I in which $R_1$ comprises a tricyclic nucleus of formula Z wherein X is —$CH_2$—CH(OH)— or —$CH_2$—C(=NOH)— may exist in isomeric i.e. d- and l- and syn- and anti-form. The present invention is not restricted to particular isomeric forms but covers any individual isomeric forms of these compounds as well as mixtures thereof.

Preferably n is 3. X is preferably —$CH_2$—$CH_2$—, —CH=CH— or —$CH_2$—CO—, more preferably —$CH_2$—CO— or —CH=CH—. A is preferably a fused thiophene ring or a fused benzene ring.

Preferred groups of compounds in accordance with the invention are those wherein $R_1$ comprises a tricyclic nucleus of formula:

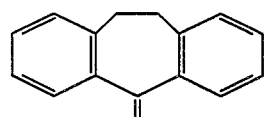

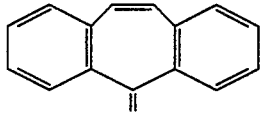

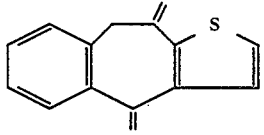

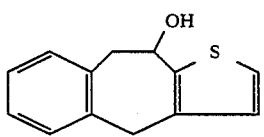

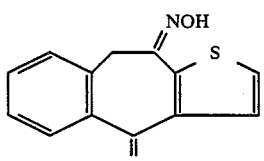

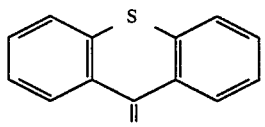

or

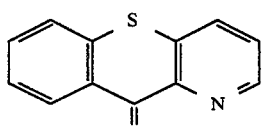

More preferably $R_1$ comprises a tricyclic nucleus of formula Za, Zb or Zc above, most preferably of formula Zb or Zc above.

The tricyclic nucleus may be substituted or unsubstituted. Suitable substituents are those known in the art for pharmaceutically active substances comprising a tricyclic ring system, in particular a tricyclic nucleus Z as defined above. Preferably the tricyclic nucleus is unsubstituted.

By the term "physiologically-hydrolysable and -acceptable acid residue" is meant an acid residue which is removable by hydrolysis under physiological conditions to yield an acid which is itself physiologically acceptable, i.e. non toxic, at the desired dosage levels. $R_2$ in formula I may accordingly represent e.g. a carboxylic acyl residue, e.g. acetyl or benzoyl, or the monoacyl residue of a dicarboxylic acid, e.g. succinic acid. Preferably $R_2$ is hydrogen.

A group of compounds in accordance with the invention comprises those of formula I wherein
n is 2 or 3,
$R_1$ is an unsubstituted tricyclic nucleus of formula Z as illustrated above in which X is —S— and A is a fused benzene or a fused pyridine ring; or X is —CH=CH— or —$CH_2$—$CH_2$— and A is a fused benzene ring; or X is —$CH_2$—CO— and X is a fused thiophene ring, and
$R_2$ is hydrogen, as well as the acid addition salts thereof.

The present invention further provides a process for the production of a compound of formula I as defined above, which comprises, (a) for the production of a compound of formula I wherein $R_2$ and n have the meanings given above and $R_1$ comprises a tricyclic nucleus of formula $Z_1$

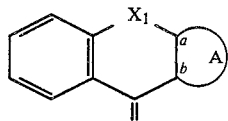

in which $X_1$ has the meaning given for X in formula Z above except that it may not represent —$CH_2$—C(=NOH)— or —$CH_2$—CH(OH) and A has the meaning given for formula Z; introducing a group of formula II

—$(CH_2$—$CH_2$—$O)_n$—H  II wherein n has the meaning given above, into a compound of formula III

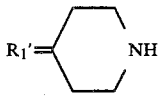

wherein $R_1'$ comprises a tricyclic nucleus of formula $Z_2$

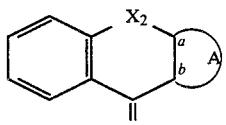

wherein $X_2$ is
(i) a group $X_1$ as defined above or (ii) a precursor thereof and A has the meaning given for formula Z, when required converting a precursor group $X_2$ into a group $X_1$ and, when required, esterifying a compound thus obtained to obtain a corresponding compound wherein $R_2$ is a physiologically-acceptable and -hydrolysable acid residue; or (b) for the production of a compound of formula I wherein $R_2$ and n have the meanings given above and $R_1$ comprises a tricyclic nucleus of formula $Z_3$

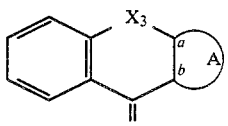

in which $X_3$ is —$CH_2$—C(=NOH)— or —$CH_2$—CH(OH)— and A has the meaning given for formula Z; converting the keto group in a compound of formula I wherein $R_2$ is hydrogen, n has the meaning given above and $R_1$ comprises a tricyclic nucleus of formula $Z_4$

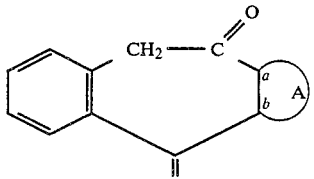

in which A has the meaning given for formula Z and, when required, esterifying a compound thus obtained to obtain a corresponding compound wherein $R_2$ is a physiologically-acceptable and -hydrolysable acid residue, and recovering the obtained compound of formula I in free base or acid addition salt form.

The introduction of the group of formula II in the compounds of formula III, according to process (a), may be effected in conventional manner for the alkylation of the nitrogen atom of cyclic amines. Preferably, the introduction is effected by reacting the compound of formula III with a compound of formula IV

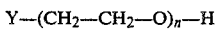
Y—$(CH_2$—$CH_2$—$O)_n$—H  IV wherein n is as defined above and Y is a leaving group, for example a halogen atom, preferably chlorine, bromine or iodine, in the presence of a solvent, for example methyl-isobutylketone, or in presence of a basic reagent, for example sodium carbonate, at temperatures from 50° C. to boiling point of the reaction mixture.

In the starting materials of formula III, $X_2$ may signify a precursor group. Suitable precursor groups are known in the art and include, for example, a group

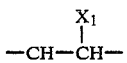

wherein $X_1$ is chlorine or bromine or a group

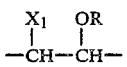

wherein $X_1$ is as defined above and R is lower alkyl, preferably methyl. These groups may be converted into groups —CH=CH— and —$CH_2$—CO— according known methods, for example as described in Belgian patent specifications Nos. 794 370 and 771 964.

The conversion of the keto group according to process (b) may be effected according known methods. For example conversion of the group —CO— into the group —CH(OH)— may conveniently be effected by reducing the keto group with a complex borohydride, for example sodium borohydride, in an inert organic solvent such as ethanol. The conversion of the group —CO— into a group —C(=NOH)— may conveniently be effected by reacting the keto group with an acid addition salt of hydroxylamine, e.g. hydroxylamine hydrochloride, according known methods.

The esterification of compounds of formula I wherein $R_2$ is hydrogen, may be effected in conventional manner, e.g. by reaction with an appropriate physiologically acceptable acid or a reactive functional derivative thereof.

The resulting compounds of formula I may be recovered from the initially obtained reaction mixture in free base or acid addition salt form, and purified in known manner. Free base forms may be converted e.g. into acid addition salt forms in conventional manner and vice versa. Suitable acids for salt formation are hydrochloric acid, hydrobromic acid, oxalic acid and fumaric acid.

Insofar as the preparation of any of the starting materials defined above is not particularly described, these are known or may be prepared in conventional manner or analogously to known methods. Compounds of formula III are described for example in "Psychopharmacological Agents", Vol. I, edited by Maxwell Gordon, Academic Press, New York (1964), in Belgian patent specification No. 764 019 and British patent specification No. 1 159 133. 10-(4-piperidylidene)-thioxanthene may be prepared from the N-alkyl-substituted derivatives, described in French Pat. No. 1 305 392, according the method described for example in the Belgian Pat. No. 764 019.

In the following Examples all temperatures are given in degrees Celsius and are uncorrected.

EXAMPLE 1

4-{1-{2-[2-(2-hydroxy-ethoxy)ethoxy]ethyl}piperidin-4-yliden}-4H-benzo[4,5]cyclohepta[1,2-b]thiophen-10-(9H)-one 6.4 g 4-(4-piperidyliden)-9-oxo-9,10-dihydro-4H-benzo[4,5]cyclohepta[1,2-b]thiophen, 3.7 g triethylenglycolmonochlorhydrine, 9 g sodium carbonate and 0.1 g potassium iodide are refluxed with stirring for 26 hours in 300 ml methyl-isobutyl-ketone. After cooling and filtration, the filtrate is evaporated and the oily residue is dissolved in 2N hydrochloric acid. The solution is washed with ether, made alkaline with cooling with a 2N solution of sodium hydroxide and extracted with ether. The organic phase is then dried over magnesium sulfate and evaporated, to give the title compound as an oil. The hydrobromide melts at 177°–178°.

The following compounds of formula

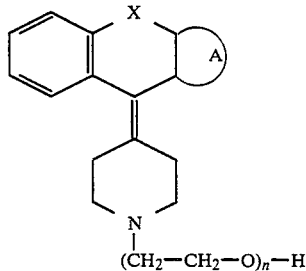

are obtained in analogous manner from the appropriate starting materials:

| Example | X | A | n | M.P. |
|---|---|---|---|---|
| 2 | —CH=CH— | ⌬ | 3 | 140–141° Hydrogenofumarate |
| 3 | —CH=CH— | ⌬ | 2 | 181–183° Hydrogenofumarate |

-continued

| Example | X | A | n | M.P. |
|---|---|---|---|---|
| 4 | —CH₂—CH₂— | ⌬ | 3 | 114–116° Oxalate |
| 5 | —CH₂—CH₂— | ⌬ | 2 | 154–155° Oxalate |
| 6 | —S— | pyridine | 2 | 167–168° Fumarate |
| 7 | —S— | ⌬ | 3 | 135–137° Fumarate |
| 8 | —S— | ⌬ | 2 | 76–77° |

EXAMPLE 9

4-{2-[2-[2-[4-(5H-dibenzo[a,d]cyclohept-5-ylidene)-piperidin-1-yl]ethoxy]ethoxy]ethoxy}-4-oxo-butanoic acid 6.0 g 2-{2-[2-[4-(5H-dibenzo[a,d]cyclohept-5-ylidene)piperidin-1-yl]ethoxy]ethoxy}-ethanol and 5 g succinic anhydride in 100 ml benzene are refluxed for 20 hours. The solvent is then distilled off, to give the title compound. The fumarate melts at 87°–90°.

EXAMPLE 10

9,10-dihydro-4-{-1[2-[2-(2-hydroxyethoxy)ethoxy]ethyl]piperidin-4-ylidene}-4H-benzo-[4,5]cyclohepta[1,2-b]thiophene-10-ol 5.8 g 4-{1-[2-[2-(2-hydroxyethoxy)ethoxy]ethyl]-piperidin-4-ylidene}-4H-benzo[4,5]cyclohepta[1,2-b]thiophene-10(9H)one hydrobromide are added with stirring to a solution of 0.5 g sodium hydroxide in 100 ml ethanol. After 15 minutes, 0.45 g sodium borhydride are added in small portions and the mixture is agitated for 20 hours at room temperature. The solvent is then distilled off, the residue is taken up with water and with sodium hydroxide solution and extracted several times with chloroform. The combined extracts are then dried and evaporated, to give the title compound as a light yellow oil. The hydrogenofumarate of the title compound melts at 110°–113°.

EXAMPLE 11

4-{1-[2-[2-(2-hydroxyethoxy)ethoxy]ethyl]piperidin-4-ylidene}-4H-benzo[4,5]cyclohepta[1,2-b]thiophen-10(9H)-one-oxime 6.0 g 4-{1-[2-[2-(2-hydroxyethoxy)ethoxy]ethyl]-piperidin-4-ylidene}-4H-benzo[4,5]cyclohepta[1,2-b]thiophen-10(9H)one and 0.95 g hydroxylaminehydrochlorid in 70 ml pyridine are refluxed for 12 hours. After elimination of the pyridine by distillation, ethanol and a little water are added to the residue and the title compound is crystallised out as the hydrochlorid (Mt. p. 240°–243°).

The compounds of formula I possess pharmacological activity. In particular, the compounds possess antianaphylactic activity, and are therefore useful in the treatment and prophylaxis of asthmatic conditions, for example exercise induced asthma and, in particular, allergic asthma, e.g. allergic bronchial asthma, as well as in the treatment or prophylaxis of other allergic disorders such as rhinitis, conjunctivitis, allergic skin reactions and allergic reactions of the gastro-intestinal tract. This activity is indicated in the passive cutaneous anaphylaxis (PCA) test in the rat.

The method employed in this test is based on those described by Mota, Immunology 7, 681 (1964) and Stofland and Share, J. Physiol. Pharmacol. 52, 1114 (1974). Female rats (180–200 g) are sensitized by subcutaneous administration of 1 mg of ovalbumin and 200 mg aluminium hydroxide, dissolved in 1 ml of physiological saline solution and intraperitoneal administration of 0.5 ml of Haemophilus pertussis vaccine (Schweizerisches Serum- und Impfinstitut, Bern, Switzerland; $4 \times 10^{10}$ organism/ml). Fourteen day later, the animals are decapited, the blood centrifuged and the serum (anti-ovalbumin serum) collected and deep frozen.

The diluted anti-ovalbumin serum is injected intradermally (0.1 ml per injection site) at three sites on the backs of untreated, female rats. Twenty-four hours after the passive sensitisation, the rats receive either solvent or the test compound i.v. in a tail-vein or per os. Immediately afterwards or, in the case of p.o. administration, 60 minutes later, the animals receive an intravenous injection of 1 ml of antigen. The antigen (5 mg/ml) is dissolved in a 0.25% solution of Evans blue dye in physiological saline. In the controls this injection elicits a cutaneous anaphylactic reaction, the intensity of which is proportional to the distance to which the dye diffuses into the tissue surrounding the four sensitisation sites. Thirty minutes later, the rats are killed in $CO_2$ and the diameter in mm of the blue spot at each injection site measured. The drug dose decreasing the diameter of the blue area by 50% compared with solvent pretreated control rats ($ED_{50}$), is obtained from the regression line. The dose-effect correlation is tested for statistical significance.

In the above test, compounds of the formula I are found to be active on administration at dosages of from about 0.1 to about 3.2 mg/kg p.o. and from about 0.056 to about 1.00 mg/kg i.v. $ED_{50}$ values for the representative compounds 4-{1-[2-[2-(2-hydroxy-ethoxy)ethoxy]ethyl]piperidin-4-yliden}-4H-benzo[4,5]cyclohepta[1,2-b]thiophen-10(9H)-one. HBr (Compound A) and 2-{2-[2-[4-(5H-dibenzo[a,d]cyclohept-5-yliden)piperidin-1-yl]ethoxy]ethoxy}ethanol hydrogenofumarate (Compound B) as well as for the reference compound 5,5'-[(2-hydroxy-1,3-propanediyl)bis-(oxy)]bis[4-oxo-4H-1-benzopyran-2-carboxylic acid] (Compound C: also known as Cromolyn, a known anti-asthmatic agent), measured in the above test are shown in the following table:

|  | $ED_{50}$ (p.o) Ca...mg/kg | $ED_{50}$ (i.v.) Ca...mg/kg |
| --- | --- | --- |
| Compound A | 1.8 | 0.21 |
| Compound B | 0.49 | 0.22 |
| Compound C | — | 2.6 |

For the above-mentioned use, the dosage will, of course, vary depending on the compound employed, mode of administration and therapy desired. However, in general, satisfactory results are obtained on administration at a daily dosage of from about 0.007 to about 0.14 mg/kg of animal body weight, conveniently administered once or in divided doses 2 to 4 times a day or in sustained release form. Preferably, administration is in unit dosage form once or twice daily. For the larger mammal, e.g. for asthmatic patients, the total daily dosage is in the range of from about 0.1 to about 10 mg, and dosage forms suitable for oral administration comprise from about 0.1 to about 10 mg preferably about 0.25 to about 0.5 mg of the compound of formula I admixed with a solid or liquid pharmaceutical carrier or diluent.

The compound may be administered in free form or e.g. in pharmaceutically acceptable acid addition salt form. Such salt forms possess the same order of activity as the free form and are readily prepared in conventional manner. Examples of suitable acids for the formation of pharmaceutically acceptable acid addition salts include hydrochloric acid, oxalic acid, fumaric acid and hydrobromic acid.

In accordance with the foregoing the present invention also provides:

(i) a pharmaceutical composition comprising a compound of formula I as hereinbefore defined, in free base or in pharmaceutically acceptable acid addition salt form together with a pharmaceutically acceptable diluent or carrier therefor, as well as (ii) a method for the treatment or prophylaxis of asthmatic conditions, in particular allergic asthma, or for the treatment or prophylaxis of other allergic disorders, e.g. as hereinbefore described, which method comprises administering to a subject in need of such treatment an effective amount of a compound of formula I as hereinbefore defined in free base or in pharmaceutically acceptable acid addition salt form.

What we claim is:

1. A compound of formula I

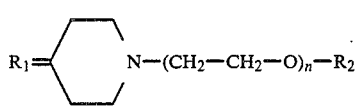

wherein n is 3,
R₁ is

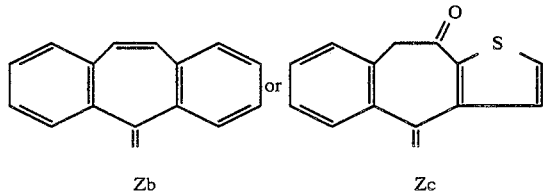

and R₂ is hydrogen or a physiologically acceptable and-hydroloysable acid residue, in free base or in pharmaceutically acceptable acid addition salt form.

2. A compound according to claim 1 wherein R₂ is hydrogen.

3. A compound according to claim 1 of the formula

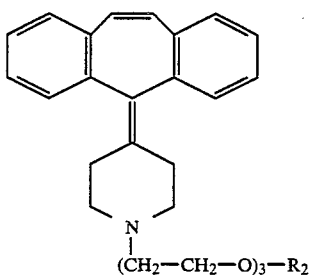

where $R_2$ is hydrogen or a physiologically-acceptable and
hydrolysable acid residue, in free base or in pharmaceutically acceptable acid addition salt form.

4. A compound according to claim 1 of the formula

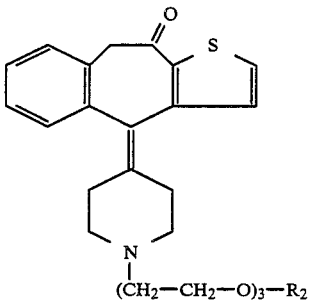

where $R_2$ is hydrogen or a physiologically-acceptable and
hydrolysable acid residue, in free base or in pharmaceutically acceptable acid addition salt form.

5. A compound according to claim 3, which is 4-{2-[2-[2-[4-(5H-dibenzo[a,d]cyclohept-5-ylidene)piperidin-1-yl]ethoxy]ethoxy]ethoxy}-4-oxo-butanoic acid.

6. A compound according to claim 4 which is 4-{1-[2-[2-(2-hydroxy-ethoxy)ethoxy]ethyl]piperidin-4-yliden}-4H-benzo[4,5]cyclohepta[1,2-b]thiophen-10-(9H)-one, in free base or in acid addition salt form.

7. A compound according to claim 3 which is 2-{2-[2-[4-(5H-dibenzo[a,d]cyclohept-5-yliden)piperidin-1-yl]ethoxy]ethoxy}ethanol, in free base or in acid addition salt form.

8. A pharmaceutical composition useful in the treatment or prophylaxis of asthma, allergic conditions, and allergic asthma comprising a compound according to claim 1 in free base or pharmaceutically acceptable acid addition salt form, in an amount effective for the treatment of asthma, allergic conditions, and allergic asthma together with a pharmaceutically acceptable diluent or carrier therefor.

9. A method for the treatment or prophylaxis of asthma in a subject in need of such treatment, which method comprises administering to said subject an effective amount of a compound according to claim 1 in free base or pharmaceutically acceptable acid addition salt form.

10. A method for the treatment or prophylaxis of allergic conditions in a subject in need of such treatment, which method comprises administering to said subject an effective amount of a compound according to claim 1 in free base or pharmaceutically acceptable acid addition salt form.

11. A method for the treatment or prophylaxis of allergic asthma in a subject in need of such treatment, which method comprises administering to said subject an effective amount of a compound according to claim 1 in free base or pharmaceutically acceptable acid addition salt form.

* * * * *